(12) United States Patent
Klee et al.

(10) Patent No.: US 9,895,294 B2
(45) Date of Patent: Feb. 20, 2018

(54) TEMPORARY ROOT CANAL SEALER DISPERSION

(75) Inventors: Joachim E. Klee, Rdolfzell (DE);
Christoph Weber, Constance (DE);
Andreas E. Grützner, Reichenau (DE)

(73) Assignee: DENTSPLY SIRONA INC., York, PA (US)

( * ) Notice: Subject to any disclaimer, the term of this patent is extended or adjusted under 35 U.S.C. 154(b) by 494 days.

(21) Appl. No.: 13/257,147

(22) PCT Filed: Mar. 18, 2010

(86) PCT No.: PCT/EP2010/001708
§ 371 (c)(1),
(2), (4) Date: Jan. 18, 2012

(87) PCT Pub. No.: WO2010/105834
PCT Pub. Date: Sep. 23, 2010

(65) Prior Publication Data
US 2012/0115982 A1    May 10, 2012

(30) Foreign Application Priority Data

Mar. 18, 2009 (EP) .................................... 09003907

(51) Int. Cl.
*A61K 6/08* (2006.01)
*A61K 6/00* (2006.01)
*A61K 6/06* (2006.01)

(52) U.S. Cl.
CPC .............. *A61K 6/0038* (2013.01); *A61K 6/06* (2013.01); *A61K 6/0681* (2013.01)

(58) Field of Classification Search
CPC ... A61K 6/0038; A61K 6/0023; A61K 6/0017
USPC ................................. 523/118, 117; 433/224
See application file for complete search history.

(56) References Cited

U.S. PATENT DOCUMENTS

| | | | |
|---|---|---|---|
| 4,288,355 A | * | 9/1981 | Anderson ............ A61K 6/0023 523/116 |
| 4,652,593 A | * | 3/1987 | Kawahara et al. ........... 523/116 |
| 4,678,436 A | * | 7/1987 | Kondo et al. ............... 433/228.1 |
| 5,540,766 A | | 7/1996 | Castellani |
| 5,624,980 A | * | 4/1997 | Kobori .............................. 524/5 |
| 2003/0199605 A1 | | 10/2003 | Fischer |
| 2008/0287566 A1 | | 11/2008 | Musikant et al. |
| 2010/0260849 A1 | * | 10/2010 | Rusin et al. .................. 424/486 |

FOREIGN PATENT DOCUMENTS

| | | |
|---|---|---|
| DE | 19961002 A1 | 7/2001 |
| EP | 0673937 A1 | 9/1995 |
| EP | 1547571 A1 | 6/2005 |
| GB | 2173207 A | 10/1986 |

\* cited by examiner

*Primary Examiner* — Michael Pepitone
(74) *Attorney, Agent, or Firm* — Leana Levin; Douglas Hura; David Zdurne (57) ABSTRACT

A temporary root canal sealer dispersion having a pH of at least 9 and comprising: (i) an aqueous dispersion medium comprising an oligomer and/or polymer having Lewis basic groups, and optionally a hydroxide of an alkali metal and/or a hydroxide of an alkaline earth metal, and (ii) a dispersed phase comprising a radio-opaque filler, wherein the weight ratio of oligomer and/or polymer having Lewis basic groups to hydroxide of an alkali metal and/or hydroxide of an alkaline earth metal is at least 0.5 when said aqueous dispersion medium comprises a hydroxide of an alkali metal and/or a hydroxide of an alkaline earth metal.

14 Claims, 2 Drawing Sheets

TEMPORARY ROOT CANAL SEALER DISPERSION

CROSS REFERENCE TO RELATED PATENT APPLICATIONS

This patent application claims priority to European Patent Application No. 09 003 907.4, which was filed Mar. 18, 2009.

FIELD OF THE INVENTION

The present invention relates to a temporary root canal sealer dispersion. Furthermore, the present invention also relates to a kit-of-parts for the formation of a temporary root canal sealer dispersion. A temporary root canal sealer dispersion has improved storage stability and improved properties such as radio-opacity and resistance against bacterial growth.

BACKGROUND OF THE INVENTION

Temporary root canal sealers are known. Conventional temporary root canal sealers comprise a strongly alkaline aqueous mixture of calcium hydroxide and a radio-opaque filler such as barium sulfate.

Temporary root canal sealers are intended to be a short-term means of cleaning and disinfecting the root canal cavity formed upon extraction of the dental pulp and/or root canal tissue, thereby preventing staining of the tooth upon effecting permanent sealing.

Temporary root canal sealers containing radio-opaque materials may be employed for obtaining information about the internal environment of pulp chamber and/or associated root canals of any given tooth.

Conventional temporary root canal sealers exhibit relatively poor radio-opacities. Moreover, conventional temporary root canal sealers are poor in storage stability since the aqueous mixture of calcium hydroxide and a radio-opaque filler become heterogenous non-uniform mixtures over time.

DE 19961002 C2 discloses a temporary root canal filling material which incorporates an X-ray contrast material, together with calcium hydroxide, an exsiccant and an organic solvent, which is an absorptive, antibacterial filler of a dry consistency, which neither hardens nor encroaches into the apical region of the root canal cavity.

U.S. Pat. No. 5,540,766 relates to a non-aqueous dental composition comprising calcium hydroxide, gutta-percha, a radio-opaque substance and a substance which adds rigidity to the composition, which is used to make thermoplastic root canal points for obturation. Summary of the Invention It is the problem of the present invention to provide a temporary root canal sealer dispersion which has improved radio-opacity, resistance against bacterial growth and consistency.

It is a further problem of the present invention to provide a temporary root canal sealer dispersion which is stable in both the oral environment and during storage.

It is a yet further problem of the present invention to provide a temporary root canal sealer dispersion which is non-toxic, anti-inflammatory and acts as a sterilant.

SUMMARY

These problems are solved according to the present invention by a temporary root canal sealer dispersion having a pH of at least 9 and comprising:

(i) an aqueous dispersion medium comprising an oligomer and/or polymer having Lewis basic groups, and optionally a hydroxide of an alkali metal and/or a hydroxide of an alkaline earth metal, and (ii) a dispersed phase comprising a radio-opaque filler, wherein the weight ratio of oligomer and/or polymer having Lewis basic groups to hydroxide of an alkali metal and/or hydroxide of an alkaline earth metal is at least 0.5 when said aqueous dispersion medium comprises a hydroxide of an alkali metal and/or a hydroxide of an alkaline earth metal.

In a first embodiment, the temporary root canal sealer dispersion comprises an aqueous dispersion medium comprising an oligomer and/or polymer having one or more Lewis basic groups, and a hydroxide of an alkali metal and/or a hydroxide of an alkaline earth metal, wherein the weight ratio of oligomer and/or polymer to hydroxide of an alkali metal and/or hydroxide of an alkaline earth metal is at least 0.5.

In a second embodiment, the aqueous dispersion medium does not comprise a hydroxide of an alkali metal and/or a hydroxide of an alkaline earth metal.

The present invention additionally provides a kit-of-parts for the formation of a temporary root canal sealer dispersion, as defined above, wherein the oligomer and/or polymer of the aqueous dispersion medium is packaged separately from the radio-opaque filler and, if comprised in said kit-of-parts, the hydroxide of an alkali metal and/or hydroxide of an alkaline earth metal and/or precursor or precursors thereof.

DETAILED DESCRIPTION OF THE INVENTION

The present invention relates to a temporary root canal sealer dispersion. The temporary root canal sealer dispersion is a sealer which is in the form of a dispersion and is suitable for temporarily sealing a root canal. The temporary root canal sealer dispersion comprises an aqueous dispersion medium and a dispersed phase.

The properties of a root canal sealer and, in particular, a temporary root canal sealer dispersion depend on many factors, but general trends can be seen between the composition of the aqueous dispersion medium and the temporary root canal sealer dispersion properties. Since the trends are not necessarily linear and there are many interactions, trends should not be extrapolated too far from known points. A change of most components in an aqueous dispersion medium affects the degree to which the dispersed phase may be incorporated therein and, hence, amongst other properties, affects the radio-opacity, sealing capacity and consistency of the temporary root canal sealer dispersion in some way. The following trends are observed in multiple regression analysis of the aqueous dispersion medium and the properties of the resulting temporary root canal sealer dispersions.

The temporary root canal sealer dispersion has a pH of at least 9. Preferably, the temporary root canal sealer dispersion has a pH of at least 11, more preferably, at least 12, still more preferably at least 13. The use of a pH of at least 9 ensures that greater amounts of dispersed phase may be incorporated into the aqueous dispersion medium than if the pH of the temporary root canal sealer dispersion were less than this value. The pH values are measured using standard pH paper such as universal indicator paper.

The aqueous dispersion medium is a medium comprising water in which a dispersed phase may be dispersed. Water may be present in the temporary root canal sealer dispersion in an amount of from 20 to 80 weight percent based on the total amount of the composition. More preferably, the water of the temporary root canal sealer dispersion is present in an amount of from 20 up to 70 weight percent, most preferably from 25 to 60 weight percent, based on the total amount of the composition. If a lower weight percent of water is employed in the aqueous dispersion medium, the temporary root canal sealer dispersion is insufficiently plastic as to be effective at sealing and maintaining the sterility of a given root canal cavity. Moreover, if a lower weight percent of water is employed in the aqueous dispersion medium, the consistency and homogeneity of the resulting temporary root canal sealer dispersion is decreased, such that the dispersion is rendered unsuitable for use as a sealer or sterilant. The reduced plasticity, consistency and homogeneity of such dispersions also renders them unsuitable for use as visualizing agents in combination with X-ray radiation. Conversely, if a greater weight percent of water is employed in the temporary root canal sealer dispersion, the remaining components thereof are effectively diluted, such that the dispersion takes on the characteristics of a solution. Consequently, dispersions comprising a greater weight percent of water are rendered too fluid to act as sealers, let alone prevent radio-opaque fillers from settling out of the dispersion, particularly when dense radio-opaque fillers are used in increased proportions.

The temporary root canal sealer dispersion comprises an oligomer having one or more Lewis basic groups and/or a polymer having one or more Lewis basic groups. A Lewis basic group comprises a lone pair of electrons which may be protonated in an aqueous medium. Nitrogen, phosphorus, oxygen and sulfur are examples of atoms which may provide a lone pair of electrons in an appropriate functional group, whereby nitrogen is preferred. Accordingly, the following functional groups containing such atoms may be used in an oligomer and/or a polymer in order to provide one or more Lewis basic groups: primary amino groups, secondary amino groups, tertiary amino groups, amido groups, hydrazino groups, phosphino groups, alkali metal salts of carboxylic acid groups, alkali alkylene oxylates and sulfur analogues thereof. The oligomer and/or polymer employed in the aqueous dispersion medium may be selected from amino-substituted polymers, amino resins and polyamines, either singly or in combination. In a preferred embodiment, the oligomer and/or polymer of the temporary root canal sealer dispersion is a polyamine. The polyamine may be selected from polyethylene imine, polypropylene imine, polybutylene imine and polyphenylene imine, either singly or in combination. In a more preferred embodiment, the oligomer and/or polymer of the temporary root canal sealer dispersion is polyethylene imine.

Preferably, the basicity of the Lewis basic group is higher than the basicity of the hydroxyl ion, whereby the pH of a neutral aqueous medium may be increased by the presence of the oligomer and/or the polymer used according to the present invention. The oligomer and/or polymer is preferably soluble in the aqueous medium of the temporary root canal sealer dispersion.

In case more than a single oligomer and/or polymer having one or more Lewis basic groups are employed in the aqueous dispersion medium, the oligomers and/or polymers are independent from each other.

In one aspect, the oligomer and the polymer are both employed in the aqueous dispersion medium as a polymer-oligomer blend.

In one aspect, the monomers of the aforementioned oligomer and/or polymer may be copolymerized with different monomers of the aforementioned oligomer and/or polymer. In an alternative aspect, the monomers of the aforementioned oligomer and/or polymer may be graft-copolymerized or block-copolymerized onto an oligomer and/or polymer comprised of different monomers. Monomers of secondary polymers suitable for the formation of copolymers are selected from the monomers of polyacrylates, polyimides, polyolefins, polystyrenes, polyesters, polyethers, polyamines, polyamidines and polyamides, and copolymerized with monomers of the aforementioned oligomer and/or polymer having Lewis basic groups. In one aspect, monomers of secondary polymers suitable for the formation of copolymers are selected from the monomers of polyacrylates, polyimides, polyolefins, polystyrenes, polyesters, polyethers, polyamines, polyamidines and polyamides, and graft-copolymerized or block-copolymerized to the aforementioned oligomer and/or polymer having Lewis basic groups. Preferably, the monomers of the secondary polymer are monomers of a strong organic base such as an amidine resin or amidine latex.

The use of any of the oligomers and/or polymers specified above allows the radio-opaque filler to be dispersed in the aqueous dispersion medium in considerable amounts without affecting the stability of the temporary root-canal sealer dispersion such that the radio-opaque filler precipitates therefrom. It is particularly preferred that the oligomer and/or polymer having Lewis basic groups is a basic polymer such as a polyamine. Employment of a basic polymer circumvents the need to incorporate excessive amounts of a hydroxide of an alkali metal and/or hydroxide of an alkaline earth metal into the temporary root canal sealer dispersion in order to maintain its pH. Moreover, use of a basic polymer supports the formation of temporary root canal sealer dispersions which are stable insofar as the radio-opaque filler is prevented from settling out of the dispersion, even in the event that a dense radio-opaque filler is dispersed therein in increased weight percent based on the total amount of the composition.

The oligomer and polymer employed in the aqueous dispersion medium share a average molecular weight range spanning between 500 and 200,000 Da. The oligomer preferably has a weight average molecular weight, $M_w$, of between 500 and 10,000 Da, more preferably between 1,000 and 10,000 Da, even more preferably between 1,000 and 9,000 Da, most preferably between 2,000 and 8,000 Da. In contrast, the polymer preferably has a weight average molecular weight, $M_w$, of between 10,000 and 200,000 Da, more preferably between 10,000 and 100,000 Da, even more preferably between 10,000 and 50,000 Da, most preferably between 20,000 and 50,000 Da.

Accordingly, when both the oligomer and the polymer are employed in the aqueous dispersion medium, the aqueous dispersion medium exhibits a bimodal average molecular weight distribution. In a preferred embodiment, the oligomer has a weight average molecular weight, $M_w$, of between 500 and 10,000 Da and the polymer has a weight average molecular weight, Mw, of between 10,000 and 200,000 Da. Preferably, the oligomer has a weight average molecular weight, Mw, of between 500 and 10,000 Da and the polymer has a weight average molecular weight, Mw, of between 10,000 and 100,000 Da. More preferably, the oligomer has a weight average molecular weight, Mw, of between 1,000 and 10,000 Da and the polymer has a weight average molecular weight, Mw, of between 10,000 and 100,000 Da. Most preferably, the oligomer has a weight average molecular weight, Mw, of between 1,000 and 10,000 Da and the polymer has a weight average molecular weight, Mw, of between 10,000 and 50,000 Da.

In the event that the average molecular weight of the polymer lies above the maximum value specified, the viscosity of the aqueous dispersion medium is so high that it not only prevents formation of a consistent temporary root canal sealer dispersion, but also prevents the radio-opaque filler from being incorporated therein. In contrast, if the average molecular weight of the oligomer lies below the minimum value specified, the viscosity of the temporary root canal sealer dispersion is so low that the radio-opaque filler settles out of the dispersion, particularly when dense radio-opaque fillers are employed in an increased weight percent based on the total amount of the composition. Moreover, if the average molecular weight of the oligomer lies below the minimum value specified, the viscosity of the temporary root canal sealer dispersion is so low that it prevents the dispersion from sealing the root canal effectively and/or for sufficient lengths of time. Under such circumstances, the temporary root canal sealer dispersion is rendered ineffective as a radio-opaque sealer. The average molecular weight, Mw, of the oligomer and/or polymer having Lewis basic groups may be determined by any method for determining the distribution in molecular weight of a macromolecule. Typical methods include size exclusion chromatographic techniques such as gel permeation chromatography or gel filtration chromatography, as well as mass spectrometric techniques such as electrospray mass spectrometry or matrix-assisted laser desorption/ionisation spectroscopy, and/or viscosity measurements. In the case where the oligomer and polymer are copolymerized with each other, the average molecular weight, Mw, of each of the oligomer and polymer may be determined using any of the above methods, in conjunction with end-group determination measurements, time-lapse experiments and multiple regression analyses. Mass spectrometric techniques such as electrospray mass spectrometry or matrix-assisted laser desorption/ionisation spectroscopy are particularly preferred for the determination of the average molecular weight, Mw, of the oligomer and/or polymer having Lewis basic groups.

In a preferred embodiment, the oligomer and/or polymer having Lewis basic groups of the temporary root canal sealer dispersion is present in an amount of from 10 to 80 weight percent based on the total amount of the composition. More preferably, the oligomer and/or polymer having Lewis basic groups of the temporary root canal sealer dispersion is present in an amount of from 20 to 70 weight percent, most preferably from 21 to 60 weight percent, based on the total amount of the composition. If a lower weight percent of oligomer and/or polymer having Lewis basic groups is employed in the aqueous dispersion medium, the temporary root canal sealer dispersion is insufficiently plastic as to be effective for sealing and maintaining the sterility of root canal cavities. Moreover, if a lower weight percent of oligomer and/or polymer having Lewis basic groups is employed in the aqueous dispersion medium, the consistency and homogeneity of the resulting temporary root canal sealer dispersion is decreased, such that the dispersion is likewise rendered unsuitable for use as a sealer or sterilant. The reduced plasticity, consistency and homogeneity also render such dispersions ineffective as visualizing agents for use in combination with X-ray radiation. Conversely, if a greater weight percent of oligomer and/or polymer having Lewis basic groups is employed in the temporary root canal sealer dispersion, the remaining components thereof are effectively diluted, such that the radio-opacity of the dispersion is likewise reduced.

The hydroxide of an alkali metal and/or hydroxide of an alkaline earth metal which may optionally be present in the temporary root canal sealer dispersion is selected from any of the hydroxides of lithium, sodium, potassium, rubidium, caesium, magnesium, calcium, strontium, barium and radium, either singly or in combination. In a preferred embodiment, the hydroxide of an alkali metal and/or hydroxide of an alkaline earth metal is selected from any of the hydroxides of sodium, potassium, caesium, calcium, strontium and barium, either singly or in combination. Most preferably, the hydroxide is the alkaline earth metal hydroxide, calcium hydroxide.

The hydroxide of an alkali metal and/or hydroxide of an alkaline earth metal may be added directly to the aqueous dispersion medium or it may be generated in situ in the aqueous environment of the aqueous dispersion medium from an appropriate precursor. Precursors suitable for the in situ generation of the hydroxide of an alkali metal and/or hydroxide of an alkaline earth metal comprise the oxides (including, where applicable, the peroxides and superoxides), carbonates and bicarbonates of the alkali metals and/or the alkaline earth metals, either singly or in combination. In a preferred embodiment, the hydroxide of an alkali metal and/or hydroxide of an alkaline earth metal is derived in situ from any of the oxides of sodium, potassium, caesium, calcium, strontium and barium, either singly or in combination. Most preferably, the hydroxide is derived in situ from the oxide of calcium.

The hydroxide of an alkali metal and/or hydroxide of an alkaline earth metal may be present in the temporary root canal sealer dispersion in the form of a solution and/or in the form of a hydrated or non-hydrated solid. Depending upon the composition of the temporary root canal sealer dispersion and, in particular, the composition of the aqueous dispersion medium, the hydroxide of an alkali metal and/or hydroxide of an alkaline earth metal is distributed between these two forms such that the aqueous dispersion medium may assume a form selected from any of an aqueous solution, aqueous suspension or aqueous paste, either singly or in combination. In the event that the hydroxide of an alkali metal and/or hydroxide of an alkaline earth metal is generated in situ, the precursor may similarly be present in the temporary root canal sealer dispersion in the form of a solution and/or in the form of a hydrated or non-hydrated solid.

The weight of the hydroxide present in the temporary root canal sealer dispersion may be derived from the sum of the amounts of hydroxide present in solution and in solid form. In a preferred embodiment, the hydroxide of an alkali metal and/or hydroxide of an alkaline earth metal is present in the temporary root canal sealer dispersion in an amount of from 1 to 40 weight percent based on the total amount of the composition. More preferably, the hydroxide of an alkali metal and/or hydroxide of an alkaline earth metal is present in the temporary root canal sealer dispersion in an amount of from 5 to 30 weight percent, most preferably in an amount of from 10 to 25 weight percent, based on the total amount of the composition.

The dispersed phase is a material which may be dispersed in the aqueous dispersion medium. The dispersed phase comprises a radio-opaque filler. The radio-opaque filler is a filler which, when compared to another material, exhibits opacity to electromagnetic radiation, in particular, X-rays. The radio-opaque filler may be selected from any of the zinc, ytterbium, yttrium, gadolinium, zirconium, strontium, tungsten, tantalum, thorium, niobium, barium, bismuth, molybdenum and lanthanum metals, alloys thereof, organometallic complexes thereof, oxides, sulfates, carbonates, halides, oxy-halides, subnitrates, tungstates and carbides thereof, iodine and inorganic iodides, either singly or in combination. In a preferred embodiment, the radio-opaque filler is selected from any of bismuth trioxide, bismuth carbonate, bismuth oxy-chloride, bismuth subnitrate, zirconium oxide, barium sulfate, barium tungstate and calcium tungstate, either singly or in combination. In an even more preferred embodiment, the radio-opaque filler is selected from barium tungstate and calcium tungstate, either singly or in combination. Preferably the radio-opaque filler is calcium tungstate.

The radio-opaque filler may be a finely divided particulate material which is comprised of crystalline, amorphous or metallic fibers, flakes, powders or colloids. Preferably, the radio-opaque filler is a finely divided powder. The particles of radio-opaque filler are sufficiently finely divided so as to render the temporary root canal sealer dispersion radio-opaque to X-rays, relative to another material. The radio-opaque filler may be present in the temporary root canal sealer dispersion in the form of a hydrated or non-hydrated solid. In the event that the radio-opaque filler is even slightly soluble in any of the other components of the temporary root canal sealer dispersion, the radio-opaque filler may also be present therein in the form of a solution.

The radio-opaque filler is present in the temporary root canal sealer dispersion in an amount sufficient as to render the temporary root canal sealer dispersion opaque to X-rays, relative to another material. In a preferred embodiment, the temporary root canal sealer dispersion has a radio-opacity of greater than 2.5 mm/mm aluminum. More preferably, the temporary root canal sealer dispersion has a radio-opacity of greater than 4 mm/mm Al, most preferably greater than 5 mm/mm Al. Radio-opacity is measured according to ISO 6876:2001.

These radio-opacities are achieved by incorporating a radio-opaque filler into the temporary root canal sealer dispersion. In a preferred embodiment, the radio-opaque filler is present in the temporary root canal sealer dispersion in an amount of from 10 to 60 weight percent based on the total amount of the composition. More preferably, the radio-opaque filler is present in the temporary root canal sealer in an amount of from 20 to 60 weight percent, most preferably 25 to 60 weight percent, based on the total amount of the composition.

Provided that the aqueous dispersion medium comprises a hydroxide of an alkali metal and/or hydroxide of an alkaline earth metal, the temporary root canal sealer dispersion has a weight ratio of oligomer and/or polymer having Lewis basic groups to hydroxide of an alkali metal and/or hydroxide of an alkaline earth metal of at least 0.5. Preferably, the temporary root canal sealer dispersion has a weight ratio of oligomer and/or polymer having Lewis basic groups to hydroxide of an alkali metal and/or hydroxide of an alkaline earth metal of at least 0.75, more preferably at least 1.0. In the event that the temporary root canal sealer dispersion has a reduced weight ratio of oligomer and/or polymer having Lewis basic groups to hydroxide of an alkali metal and/or hydroxide of an alkaline earth metal, insufficient proportions of oligomer and/or polymer having Lewis basic groups are present as to prevent the radio-opaque filler from settling out of the dispersion, particularly when the radio-opaque filler is dense or incorporated in an increased weight percent based on the total amount of the composition. The inherent instability of temporary root canal sealer dispersions which have a reduced weight ratio of oligomer and/or polymer having Lewis basic groups to hydroxide of an alkali metal and/or hydroxide of an alkaline earth metal not only tends to mean such dispersions lack consistency but also that such dispersions are insufficiently plastic as to seal the root canal effectively and/or for sufficient lengths of time. Under such circumstances, the temporary root canal sealer dispersion is rendered ineffective as a radio-opaque sealer.

In a preferred embodiment, the temporary root canal sealer dispersion has a weight ratio of oligomer and/or polymer having Lewis basic groups and hydroxide of an alkali metal and/or hydroxide of an alkaline earth metal to radio-opaque filler of between 0.1 and 10. Preferably, the temporary root canal sealer dispersion has a weight ratio of oligomer and/or polymer having Lewis basic groups and hydroxide of an alkali metal and/or hydroxide of an alkaline earth metal to radio-opaque filler of between 0.3 and 5, more preferably between 0.45 and 2. In the event that the weight ratio of oligomer and/or polymer having Lewis basic groups and hydroxide of an alkali metal and/or hydroxide of an alkaline earth metal to radio-opaque filler is decreased, the excessive amounts of radio-opaque filler settle out of the temporary root canal sealer dispersion, thus rendering it unstable. In contrast, if the weight ratio of oligomer and/or polymer having Lewis basic groups and hydroxide of an alkali metal and/or hydroxide of an alkaline earth metal to radio-opaque filler is increased, the temporary root canal sealer dispersion is insufficiently radio-opaque as to be effective as a visualizing agent for use in combination with X-ray radiation.

In a preferred embodiment, the temporary root canal sealer dispersion has a weight ratio of radio-opaque filler to oligomer and/or polymer having Lewis basic groups of at least 0.75. Preferably, the temporary root canal sealer dispersion has a weight ratio of radio-opaque filler to oligomer and/or polymer having Lewis basic groups of at least 0.9, more preferably at least 1.0. In the event that the weight ratio of radio-opaque filler is reduced relative to the oligomer and/or polymer having Lewis basic groups, the resulting temporary root canal sealer dispersion is rendered insufficiently radio-opaque as to be effective as a visualizing agent for use in root canal therapy in combination with X-ray radiation.

The temporary root canal sealer dispersion may additionally comprise further components which may be present in either or both of the aqueous dispersion medium and the dispersed phase.

In a preferred embodiment, the aqueous dispersion medium of the temporary root canal sealer dispersion additionally contains an antiseptic. The antiseptic may be selected from antibiotics, bactericide and bacteriostatins. More specifically, the antiseptic may be selected from aqueous solutions of an alcohol or mixtures of alcohols such as ethanol, propanol and isopropanol as 60 to 90%, 60 to 70% and 70 to 80% by volume aqueous solutions, respectively; quaternary ammonium compounds such as octenidine dihydrochloride, benzalkonium chloride, cetyltrimethylammonium bromide, cetylpyridinium chloride and benzethonium chloride; phenols such as phenol, trichlorophenol, thymol, carvacrol, triclosan and chloroxylenol; iodophors such as aqueous and/or alcoholic solutions of iodine, iodoform and povidone-iodine; aqueous solutions of inorganic compounds such as sodium chloride, sodium hydroxide, sodium bisulfate, sodium hypochlorite, calcium hypochlorite and hydrogen peroxide; and chlorhexidine-based antiseptics such as chlorhexidine, chlorhexidine dihydrochloride, chlorhexidine acetate and chlorhexidine gluconate, either singly or in combination. More preferably, the antiseptic is a chlorhexidine-based antiseptic. In a preferred embodiment, the antiseptic is chlorhexidine.

The antiseptic is incorporated into the temporary root canal sealer dispersion in order to prevent bacterial infection of the root canal cavity from occurring either during the time that the temporary root canal sealer dispersion is in place, or at any point subsequent to the filling of the cavity with a permanent sealer, filling or point. In order to circumvent bacterial infection from occurring during the time in which either the temporary root canal sealer dispersion or a permanent sealer is in place, sufficient amounts of the antiseptic are incorporated into the temporary root canal sealer dispersion so as to sterilize the root canal and maintain it in this condition for the duration that the root canal is temporarily sealed, even in the event that some of the antiseptic is leached from the sealer by diffusion into the oral environment.

In order to ensure that bacterial infection has not occurred during the time that the temporary root canal sealer dispersion is in place, an indicator may be incorporated into the temporary root canal sealer dispersion. In a preferred embodiment, the aqueous dispersion medium of the temporary root canal sealer dispersion, additionally contains a pH-indicator. The pH-indicator measures the effectiveness with which any given root canal cavity is temporarily sealed, based on a decrease in pH associated with bacterial growth in the temporarily sealed root canal cavity. As such, prior to undergoing permanent sealing the sterility of any given root canal cavity may be assessed by removing the temporary root canal sealer dispersion from said root canal cavity and determining its pH based on the pH-indicator incorporated therein. The pH-indicator may be selected from any of thymol blue, phenolphthalein, thymolphthalein, naphtholphthalein, alizarin yellow R, leucomalachite green and cresol red. In a preferred embodiment, the pH-indicator is thymol blue. The effectiveness with which a temporary root canal sealer dispersion comprising a pH-indicator has sealed and sterilised any given root canal cavity may be determined by examination of the surfaces of the temporary root canal sealer dispersion which were in contact with the internal surfaces of the cavity for the duration of the temporary sealing. In the case of a temporary root canal sealer comprising thymol blue, those surfaces of the dispersion which exhibit bacterial growth will have changed from blue to colorless due to localized decreases in the pH at sites of bacterial growth.

In a preferred embodiment, the aqueous dispersion medium of the temporary root canal sealer dispersion additionally contains a humectant. The humectants employed in the present invention may be selected from hygroscopic inorganic compounds such as lithium chloride and calcium chloride; alcohols such as methanol ethanol and isopropanol; ureas such as urea and allantoin; alkylene glycols such as ethylene glycol and propylene glycol; polysaccharides such as polydextrose; polyalkylene glycols such as polypropylene glycol, poly(tetramethylene ether)glycol and polyethylene glycol; and sugar alcohols such as glycol, glycerol, threitol, erythritol, arabitol, xylitol, ribitol, mannitol, dulcitol, iditol, lactitol, isomalt, maltitol and sorbitol, as well as glycosides, ethers amines and esters thereof such as triacetin, either singly or in combination. In a preferred embodiment, the humectant of the temporary root canal sealer dispersion is sorbitol.

In the event that the humectant comprises a polysaccharide and/or a polyalkylene glycol, the average molecular weight, Mw, of the polysaccharide and/or polyalkylene glycol is preferably less than 500 Da, more preferably less than 480 Da, most preferably less than 450 Da. The use of a polysaccharide and/or a polyalkylene glycol which has a weight average molecular weight greater than these values tends to be ineffective as a humectant. In the case of the polyalkylene glycols, this is reflected in the fact that as the average molecular weight increases, the hydroxyl value and, hence, the humectant properties decreases. In the event that a polyalkylene glycol is used as a humectant, the hydroxyl value of the polyalkylene glycol is preferably no less than 115 mg KOH/g, more preferably no less than 125 mg KOH/g, more preferably no less than 220 mg KOH/g. The humectant may be present in the temporary root canal sealer dispersion in the form of a hydrated or non-hydrated solid or liquid. In the event that the humectant is even slightly soluble in any of the other components of the temporary root canal sealer dispersion, the humectant may also be present therein in the form of a solution.

The humectant may be present in the temporary root canal sealer dispersion, in an amount of from 1 to 10 weight percent, preferably in an amount of from 1 to 5 weight percent, more preferably 1 to 3 weight percent, based on the total amount of the composition. Provided that the humectant is employed in these proportions, the moisture inherent to the aqueous dispersion medium is retained during storage of the temporary root canal sealer dispersion or, in the event that it is stored separately from the radio-opaque filler, the aqueous dispersion medium. This is to prevent the aqueous dispersion medium from solidifying or becoming so viscous prior to mixing with the radio-opaque filler that the plasticity, consistency and homogeneity of the resulting temporary root canal sealer dispersion is decreased, thereby rendering the dispersion unsuitable for use as a sealer, sterilant or visualizing material. Moreover, it is not advantageous to employ greater amounts of humectant than specified above, since this lowers the viscosity and, hence, the sealing capabilities of the temporary root canal sealer dispersion.

In addition to water, the temporary root canal sealer dispersion may additionally contain an organic solvent. The organic solvent may be selected from alcohols, esters, ethers and ketones, either singly or in combination. Preferably the solvent is a linear, branched or cyclic alkyl alcohol, or an ether or ester thereof. More preferably, the solvent is selected from methanol, ethanol, propanol, butanol, pentanol, hexanol and, where applicable, the branched or cyclic isomers thereof, and esters and ethers thereof, either singly or in combination.

The temporary root canal sealer dispersion may additionally comprise a strong organic base or strong organic acid, or a salt thereof for adjusting the pH of the composition. The strong organic base may be an amine base or amidine base such as an amidine resin or an amidine latex. The strong organic base or strong organic acid may be present in up to 20% by weight of the oligomer and/or polymer having Lewis basic groups.

The temporary root canal sealer dispersion may additionally comprise a filler other than the radio-opaque filler. The filler may be a finely divided particulate material which is comprised of crystalline, amorphous or metallic fibers, flakes, powders or colloids. Preferably, the filler comprises particles selected from silica gel granules, alumina granules, carbon fibers, and metallic, mineral, latex, resin, nylon, cellulose, polyester, polyolefin, polyacrylic, polyamide, polyalkylene, polyamide and polyacrylamide fibers and/or granules, either singly or in combination, which are dispersed in the aqueous dispersion medium. Preferably the filler comprises particles of silica. The filler may be present in the temporary root canal sealer dispersion in the form of a hydrated or non-hydrated solid. In the event that the filler is even slightly soluble in any of the other components of the temporary root canal sealer dispersion, the filler may also be present therein in the form of a solution.

The present invention also relates to a kit-of-parts for the formation of the temporary root canal sealer dispersion of the present invention. The kit-of-parts comprises at least two separate packages, wherein the oligomer and/or polymer having Lewis basic groups of the aqueous dispersion medium is packaged separately from the radio-opaque filler and, if comprised in said kit-of-parts, the hydroxide of an alkali metal and/or hydroxide of an alkaline earth metal and/or precursor or precursors thereof. In other words, the oligomer and/or polymer having Lewis basic groups of the aqueous dispersion medium is packaged in one package and the radio-opaque filler is packaged in a second package.

In the event that the kit-of-parts further comprises a hydroxide of an alkali metal and/or a hydroxide of an alkaline earth metal and/or precursor or precursors thereof, the hydroxide may be packaged with the radio-opaque filler. Alternatively, the radio-opaque filler may be packaged separately from the hydroxide of an alkali metal and/or hydroxide of an alkaline earth metal and/or precursor or precursors thereof. Further components of the temporary root canal sealer dispersion such as the pH-indicator and/or antiseptic may also be packaged separately, depending on their stability and/or shelf-life.

Mixing of the contents of the individual packages comprising the kit-of-parts will result in the formation of the temporary root canal sealer dispersion of the present invention. Mixing may be performed using any technique such as hand spatulation, mechanical mixing or static mixing, that serves to evenly disperse the dispersed phase in the aqueous dispersion medium and provide a temporary root canal sealer dispersion which exhibits consistency. The present invention will now be described with reference to Examples which are provided by way of reference.

EXPERIMENTAL SECTION

In the following Examples and Tables, all percentages are by weight, unless otherwise stated. Furthermore, the polyethylene imine employed in the following experiments, has a number-average molecular weight, Mn, of 1800 and a weight-average molecular mass, Mw, of 2000. Additionally, the calcium hydroxide employed in the following experiments has an assay of >96%, whilst calcium tungstate has a grain size of 6.4 μm and bismuth oxy-chloride is used as 99% pure material with a density of 7.72 g/mL.

Example 1

A solution of polyethylene imine (10 g) in water (10 g) was combined with calcium tungstate (12 g) and calcium hydroxide (10 g) and spatulated at root temperature for approximately 5 minutes to afford a temporary root canal filler dispersion.

Example 2

A solution of polyethylene imine (10 g) in water (10 g) was combined with calcium tungstate (20.13 g) and calcium hydroxide (10 g) and spatulated at root temperature for approximately 5 minutes to afford a temporary root canal filler dispersion.

Example 3

A solution of polyethylene imine (7.645 g) in water (7.645 g) was combined with bismuth oxychloride (10 g) and calcium hydroxide (10 g) and spatulated at root temperature for approximately 5 minutes to afford a temporary root canal filler dispersion.

Example 4

A solution of polyethylene imine (15 g) in water (15 g) was combined with calcium tungstate (45 g) and calcium hydroxide (25 g) and spatulated at root temperature for approximately 5 minutes to afford a temporary root canal filler dispersion.

Example 5

A solution of polyethylene imine (10 g) in water (10 g) was combined with calcium tungstate (10 g) and calcium hydroxide (10 g) and spatulated at root temperature for approximately 5 minutes to afford a temporary root canal filler dispersion.

The compositions of the temporary root canal sealer dispersions of Examples 1 to 5 are tabulated in Table 1 (below).

TABLE 1

| Example No. | Substance | CAS No. | Weight (g) | Content (wt. %) |
|---|---|---|---|---|
| Example 1 | Polyethyleneimine (50% in $H_2O$) | PEI 9002-98-6 | 20.00 | 47.62 |
| | Calcium tungstate | $CaWO_4$ 7790-75-2 | 12.00 | 28.57 |
| | Calcium hydroxide | $Ca(OH)_2$ 13050-62-0 | 10.00 | 23.81 |
| | Sum | | 42.00 | 100.00 |
| Example 2 | Polyethyleneimine (50% in $H_2O$) | PEI 9002-98-6 | 20.00 | 39.89 |
| | Calcium tungstate | $CaWO_4$ 7790-75-2 | 20.13 | 40.16 |
| | Calcium hydroxide | $Ca(OH)_2$ 13050-62-0 | 10.00 | 19.95 |
| | Sum | | 50.13 | 100.00 |
| Example 3 | Polyethyleneimine (50% in $H_2O$) | PEI 9002-98-6 | 15.29 | 43.33 |
| | Bismuth oxy-chloride | BiOCl 7787-59-9 | 10.00 | 28.33 |
| | Calcium hydroxide | $Ca(OH)_2$ 13050-62-0 | 10.00 | 28.33 |
| | Sum | | 35.29 | 100.00 |
| Example 4 | Polyethyleneimine (50% in $H_2O$) | PEI 9002-98-6 | 30.00 | 30.00 |
| | Calcium tungstate | $CaWO_4$ 7790-75-2 | 45.00 | 45.00 |

TABLE 1-continued

| Example No. | Substance | CAS No. | Weight (g) | Content (wt. %) |
|---|---|---|---|---|
| | Calcium hydroxide | Ca(OH)$_2$ 13050-62-0 | 25.00 | 25.00 |
| | Sum | | 100.00 | 100.00 |
| Example 5 | Polyethyleneimine (50% in H$_2$O) | PEI 9002-98-6 | 20.00 | 50.00 |
| | Calcium tungstate | CaWO$_4$ 7790-75-2 | 10.00 | 25.00 |
| | Calcium hydroxide | Ca(OH)$_2$ 13050-62-0 | 10.00 | 25.00 |
| | Sum | | 40.00 | 100.00 |

The temporary root canal sealer dispersions of Examples 1 to 4 were compared with commercially available temporary root canal sealers in terms of their radio-opacity, sealing capacity (measured as film thickness), consistency, extrudability and pH value (measured using standard pH paper such as universal indicator paper). Radio-opacity, consistency and film thickness are measured according to ISO 6876:2001. The results of these experiments are tabulated in Table 2 and represented graphically in FIGS. 1 to 4.

TABLE 2

| Product | Producer | Radio-opacity (mm/mm Al) | pH | Consistency (mm) | Film thickness (μm) |
|---|---|---|---|---|---|
| Hypocal | Merz Dental | 0.79 ± 0.021 | 9 | 17.7 ± 0.41 | |
| Pulpomixine | Septodont | 0.33 ± 0.006 | 13 | 19.5 ± 2.59 | |
| Calasept | Speiko | 0.96 ± 0.0003 | 13 | 10.9 ± 0.69 | |
| Calipro | Lege artis | 0.80 ± 0.021 | 13 | | |
| Calcipro (10 mg) + H$_2$O (10 μL) | | 1.02 ± 0.111 | | 13.0 ± 4.44 | |
| Calxyl | VOCO | 1.59 ± 0.005 | 12 | 12.7 ± 1.33 | 43 |
| Calcicur | VOCO | 0.83 ± 0.007 | 14 | 22.3 ± 0.88 | |
| Ledermix Tube | Riemser | 1.07 ± 0.156 | 7 | 23.6 ± 1.36 | 6 |
| Ledermix Paste | Riemser | 0.96 ± 0.067 | | | 15 |
| Ultra Cal XS | Ultradent | 1.37 ± 0.040 | 13 | 17.9 ± 0.66 | |
| Asphaline | Becht | 2.53 ± 0.518 | 5 | 15.7 ± 0.88 | 16 |
| Meta Paste | Meta Biomed | 1.74 | 14 | 11.8 ± 0.69 | 11 |
| Example 1 | HSS | 2.73 ± 0.032 | 13 | 23.3 ± 1.47 | 21 |
| Example 2 | HSS | 6.49 ± 0.270 | 13 | 18.4 | 25 |
| Example 3 | HSS | 5.23 ± 0.084 | 13 | 16.8 | 27 |
| Example 4 | HSS | 6.2 | 14 | 19.2 | 30 |
| Median | | 1.89 | 12 | 17.34 | 21.56 |
| Std. dev. | | 0.55 | 3 | 4.21 | 12.89 |

Figure 1:
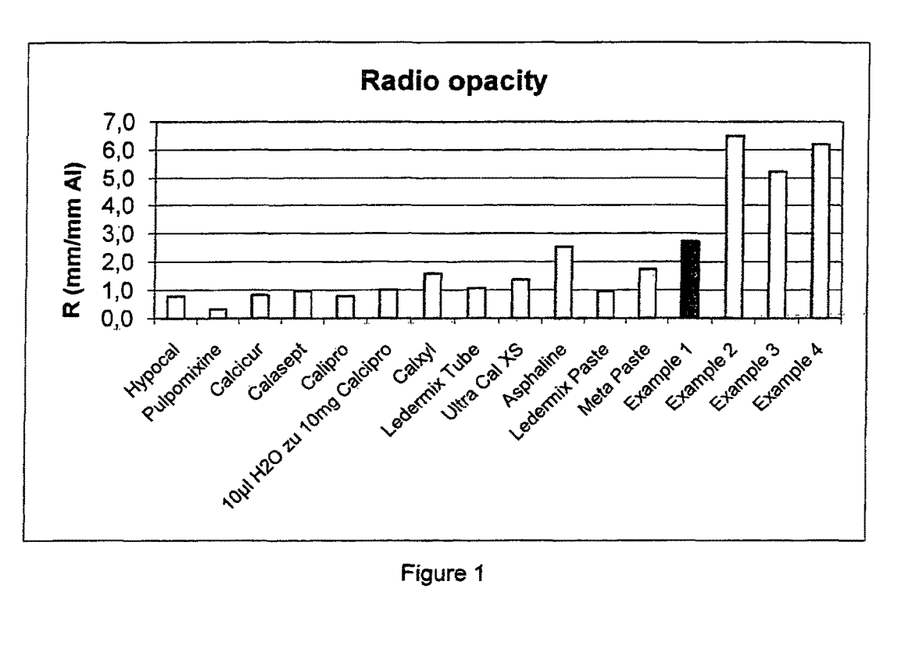
FIG. 1 shows the radio-opacity of a temporary root canal sealer dispersion described herein.

FIG. 1 shows that the radio-opacity of each of the temporary root canal sealer dispersions of Examples 1 to 4 is in the range of 2.73 to 6.49 mm/mm of aluminium. Accordingly, the temporary root canal sealer dispersions of Examples 1 to 4 exhibit superior radio-opacity in comparison to commercially available temporary root canal sealers.

Figure 2:
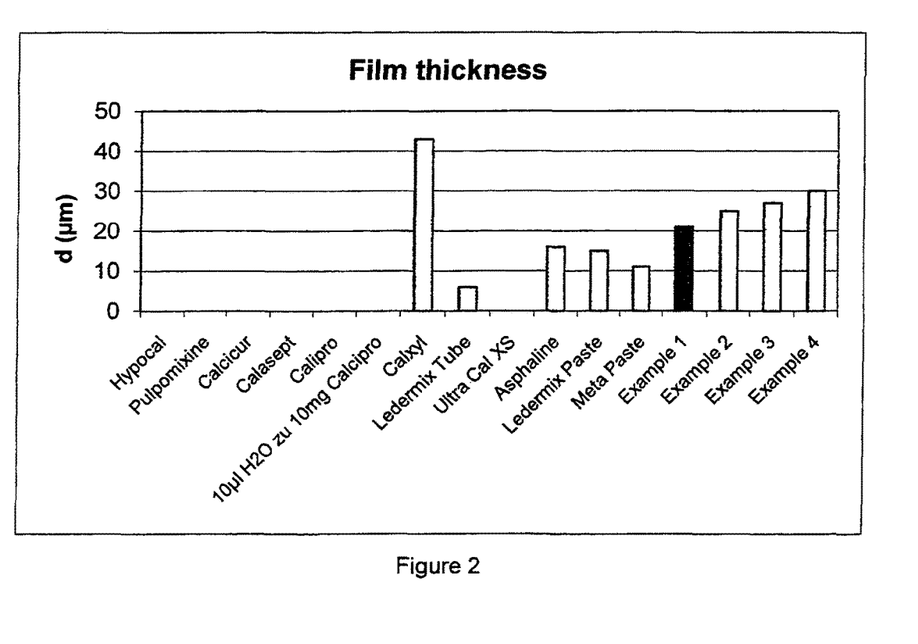
FIG. 2 demonstrates that the temporary root canal sealer dispersion described herein generates a surface film.

FIG. 2 shows that application of each of the temporary root canal sealer dispersions of Examples 1 to 4 to a surface generates films with thicknesses in the range of 21 to 30 μm. Accordingly, the temporary root canal sealer dispersions of Examples 1 to 4 exhibit superior sealing capacity in comparison to commercially available temporary root canal sealers, with the exception of that marketed as Calxyl which exhibits poor radio-opacity.

Figure 3:
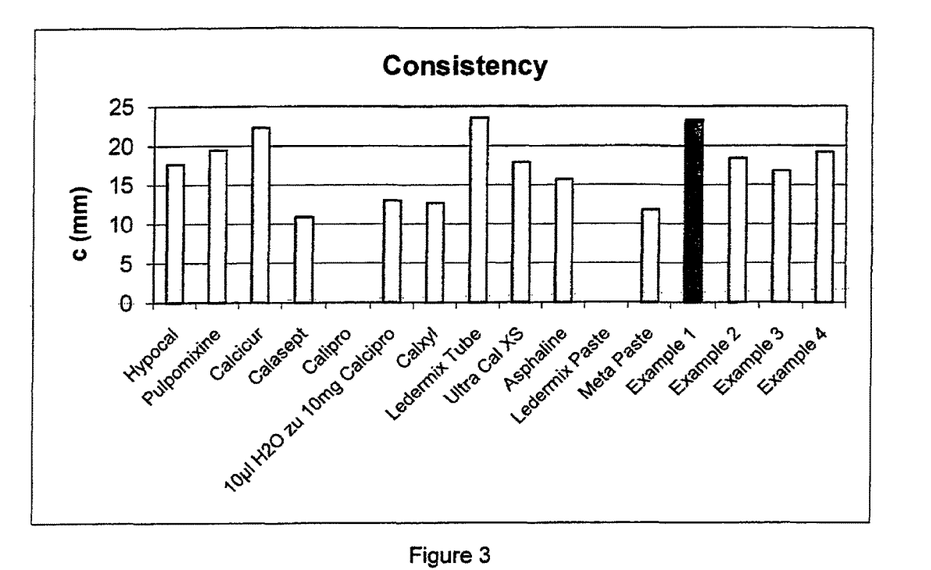
FIG. 3 demonstrates the consistency of the temporary root canal sealer dispersion described herein.
Figure 4:
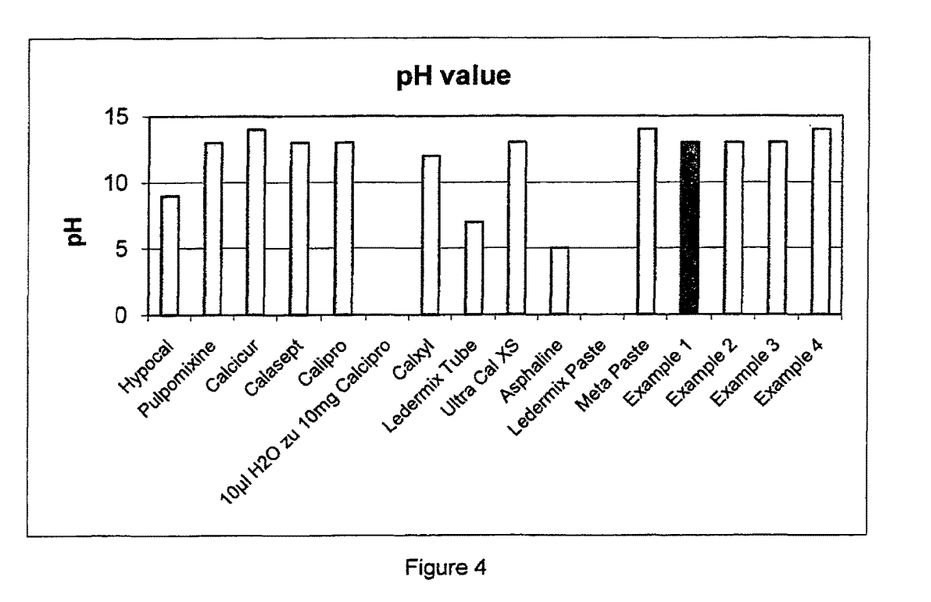
FIG. 4 shows the pH value of the temporary root canal sealer dispersion described herein.

FIG. 3 shows that the consistency of each of the temporary root canal sealer dispersions of Examples 1 to 4 is in the range of 16.8 to 23.3 mm and is therefore comparable with that of commercially available temporary root canal sealers. Similarly, FIG. 4 shows that the pH value of each of the temporary root canal sealer dispersions of Examples 1 to 4 is in the range of 13 to 14 pH units and is therefore comparable with that of commercially available temporary root canal sealers which predominantly exhibit pH values in this range. Column 6 of Table 2 additionally shows that the force required to extrude the temporary root canal sealer dispersion of Example 1 is comparable to that required to extrude a commercially available calcium hydroxy paste.

Therefore, the temporary root canal sealer dispersions of Examples 1 to 4 exhibit outstanding radio-opacity and sealing capacity in comparison to commercially available temporary root canal sealers, whilst also maintaining the plasticity, consistency and ease of application necessary for sealing and visualising any given root canal cavity. The following Examples 6 to 11 relate to two versions of temporary root canal sealer dispersion, namely a powder-liquid version and a paste version. The powder-liquid version of the temporary root canal sealer dispersion may comprise either calcium oxide and/or calcium hydroxide mixed with barium tungstate and/or calcium tungstate and an oligomer and/or polymer having Lewis basic groups and water in appropriate proportions. Alternatively, the powder-liquid version may comprise chlorhexidine mixed with barium tungstate and/or calcium tungstate and an aqueous dispersion medium comprising an oligomer and/or a polymer and a hydroxide of an alkali metal and/or hydroxide of an alkaline earth metal in approporiate proportions. Each of the temporary root canal sealer dispersion which are in powder-liquid form may be packaged in a two-component blister package, whereby the powder and liquid components are packaged in separate compartments thereof. The paste version of the temporary root canal sealer dispersion may comprise calcium oxide and/or calcium hydroxide mixed with barium tungstate and/or calcium tungstate and an aqueous solution of polyethylene glycol and/or an aqueous solution of a polymer. Alternatively, the paste version may comprise chlorhexidine mixed with barium tungstate and/or calcium tungstate and an aqueous dispersion medium comprising an aqueous solution of polyethylene glycol and/or an aqueous solution of a polymer and a hydroxide of an alkali metal and/or hydroxide of an alkaline earth metal in approporiate proportions. Alternatively, the paste may comprise barium tungstate and/or calcium tungstate and an aqueous dispersion medium comprising a strong organic base such as an amine or amidine, or a strong organic acid such as 2-acrylamido-2-methylpropanesulfonic acid mixed with an aqueous solution of polyethylene glycol and/or an aqueous solution of a polymer and a hydroxide of an alkali metal and/or hydroxide of an alkaline earth metal in appropriate proportions. Each of the temporary root canal sealer dispersion which are in paste form may be applied by means of a syringe and needle or compule.

Example 6 (Powder-Liquid Version as Kit-of-Parts)

Each compartment of a two-component blister package in which a solution of polyethylene imine (10 g) in water (10 g) was packaged in one compartment thereof and an admixture of calcium hydroxide (10 g) and calcium tungstate (20.13 g) was packaged in the other compartment thereof was opened. The solution of polyethylene imine in water and the admixture of calcium hydroxide and calcium tungstate were spatulated at root temperature for approximately 5 minutes to afford a temporary root canal filler dispersion.

Example 7 (Powder-Liquid Version as Kit-of-Parts)

Each compartment of a two-component blister package in which a solution of polyethylene imine (10 g) in water (12.4 g) was packaged in one compartment thereof and an admixture of calcium oxide (7.57 g) and calcium tungstate (20.13 g) was packaged in the other compartment thereof was opened. The solution of polyethylene imine in water and the admixture of calcium oxide and calcium tungstate were spatulated at root temperature for approximately 5 minutes to afford a temporary root canal filler dispersion.

Example 8 (Powder-Liquid Version as Kit-of-Parts)

Each compartment of a two-component blister package in which a solution of polyethylene imine (10 g) in water (10 g) was packaged in one compartment thereof and an admixture of calcium hydroxide (10 g) and barium tungstate (26.93 g) was packaged in the other compartment thereof was opened. The solution of polyethylene imine in water and the admixture of calcium hydroxide and barium tungstate were spatulated at root temperature for approximately 5 minutes to afford a temporary root canal filler dispersion.

Example 9 (Powder-Liquid Version as Kit-of-Parts)

Each compartment of a two-component blister package in which a solution of polyethylene imine (10 g) in water (12.4 g) was packaged in one compartment thereof and an admixture of calcium oxide (7.57 g) and barium tungstate (26.93 g) was packaged in the other compartment thereof was opened. The solution of polyethylene imine in water and the admixture of calcium oxide and barium tungstate were spatulated at root temperature for approximately 5 minutes to afford a temporary root canal filler dispersion.

Example 10 (Powder-Liquid Version as Kit-of-Parts)

Each compartment of a two-component blister package in which a solution of chlorhexidine (1 g) and polyethylene imine (10 g) in water (10 g) was packaged in one compartment thereof and an admixture of calcium hydroxide (10 g) and calcium tungstate (20.13 g) was packaged in the other compartment thereof was opened. The solution of polyethylene imine in water and the admixture of calcium hydroxide and calcium tungstate were spatulated at root temperature for approximately 5 minutes to afford a temporary root canal filler dispersion.

Example 11 (Powder-Liquid Version as Kit-of-Parts)

Each compartment of a two-component blister package in which a solution of chlorhexidine (1 g) and polyethylene imine (10 g) in water (10 g) was packaged in one compartment thereof and an admixture of calcium hydroxide (10 g) and barium tungstate (26.93 g) was packaged in the other compartment thereof was opened. The solution of polyethylene imine in water and the admixture of calcium hydroxide and calcium tungstate were spatulated at root temperature for approximately 5 minutes to afford a temporary root canal filler dispersion.

Each of the temporary root canal filler dispersions of Examples 6 to 11 exhibited properties comparable to the temporary root canal filler dispersions of Examples 1 to 4 and was able to be administered from a syringe or compule. In particular, the temporary root canal filler dispersions of Examples 10 and 11 not only exhibit high radio-opacity and sealing capacity, but also are antiseptic.

Thus, a root canal sealer dispersion comprising: (i) an aqueous dispersion medium comprising an oligomer and/or polymer having Lewis basic groups, and optionally a hydroxide of an alkali metal and/or a hydroxide of an alkaline earth metal, and (ii) a dispersed phase comprising a radio-opaque filler, wherein the weight ratio of oligomer and/or polymer having Lewis basic groups to hydroxide of an alkali metal and/or hydroxide of an alkaline earth metal is at least 0.5 when said aqueous dispersion medium comprises a hydroxide of an alkali metal and/or a hydroxide of an alkaline earth metal, exhibits outstanding radio-opacity and sealing capacity in comparison to commercially available temporary root canal sealers, whilst also maintaining the plasticity, consistency and ease of application necessary for sealing and visualising any given root canal cavity, preferably as a temporary root canal sealer dispersion.

What is claimed is:

1. A temporary root canal sealer dispersion comprising:
   (i) an aqueous dispersion medium comprising an oligomer and/or polymer having Lewis basic groups, where the oligomer and/or polymer is a polyamine, and optionally a hydroxide of an alkali metal and/or a hydroxide of an alkaline earth metal, and
   (ii) a dispersed phase comprising a radio-opaque filler, wherein the weight ratio of oligomer and/or polymer having Lewis basic groups to hydroxide of an alkali metal and/or hydroxide of an alkaline earth metal is at least 0.5 when said aqueous dispersion medium comprises a hydroxide of an alkali metal and/or a hydroxide of an alkaline earth metal,
   wherein the temporary root canal sealer dispersion has a pH of at least 9,
   wherein oligomer has a weight average molecular weight, Mw, of between 500 and 10,000 Da and the polymer has a weight average molecular weight, Mw, of between 10,000 and 200,000 Da,
   wherein the oligomer and/or polymer is present in an amount of from 25 to 60 weight percent based on the total amount of the composition,
   wherein the radio-opaque filler is present in an amount of from 10 to 60 weight percent based on the total amount of the composition, and wherein water is present in an amount of from 20 to 80 weight percent based on the total amount of the composition.

2. The temporary root canal sealer dispersion of claim 1, wherein the weight ratio of oligomer and/or polymer and hydroxide of an alkali metal and/or hydroxide of an alkaline earth metal to radio-opaque filler is between 0.1 and 10.

3. The temporary root canal sealer dispersion of any of claim 1, wherein the weight ratio of radio-opaque filler to oligomer and/or polymer is at least 0.75.

4. The temporary root canal sealer dispersion of claim 1, wherein the hydroxide of an alkali metal and/or hydroxide of an alkaline earth metal is selected from any of the hydroxides of sodium, potassium, caesium, calcium, strontium and barium, either singly or in combination, or wherein the hydroxide of an alkali metal and/or hydroxide of an alkaline earth metal is derived in situ from a precursor selected from any of the oxides of sodium, potassium, caesium, calcium, strontium and barium, either singly or in combination.

5. The temporary root canal sealer dispersion of claim 1, wherein the hydroxide of an alkali metal and/or hydroxide of an alkaline earth metal is present in an amount of from 1 to 40 weight percent based on the total amount of the composition.

6. The temporary root canal sealer dispersion of claim 1, wherein the radio-opaque filler is selected from any of bismuth trioxide, bismuth carbonate, bismuth oxy-chloride, bismuth subnitrate, zirconium oxide, barium sulfate, barium tungstate and calcium tungstate, either singly or in combination.

7. The temporary root canal sealer dispersion of claim 1, which has a radio-opacity of greater than 2.5 mm/mm aluminum.

8. The temporary root canal sealer dispersion of claim 1, wherein the aqueous dispersion medium additionally contains an antiseptic.

9. The temporary root canal sealer dispersion of claim 1, wherein the aqueous dispersion medium additionally contains a pH-indicator.

10. The temporary root canal sealer dispersion of any of the preceding claims, wherein the aqueous dispersion medium additionally contains a humectant.

11. A kit-of-parts for the formation of the temporary root canal sealer dispersion according to claim 1, wherein the oligomer and/or polymer of the aqueous dispersion medium is packaged separately from the radio-opaque filler and, if comprised in said kit-of-parts, the hydroxide of an alkali metal and/or hydroxide of an alkaline earth metal and/or precursor or precursors thereof.

12. The temporary root canal sealer dispersion of claim 8, wherein the antiseptic is chlorhexidine.

13. The temporary root canal sealer dispersion of claim 9, wherein the pH-indicator is thymol blue.

14. The temporary root canal sealer dispersion of claim 10, wherein the humectant is sorbitol.

* * * * *